US012373085B2

(12) United States Patent
Narvaez

(10) Patent No.: US 12,373,085 B2
(45) Date of Patent: Jul. 29, 2025

(54) LINKING GRAPH

(71) Applicant: CERNER INNOVATION, INC., Kansas City, KS (US)

(72) Inventor: Juan David Narvaez, Kansas City, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 63 days.

(21) Appl. No.: 17/471,368

(22) Filed: Sep. 10, 2021

(65) Prior Publication Data

US 2023/0084352 A1 Mar. 16, 2023

(51) Int. Cl.
*G16H 30/20* (2018.01)
*G06F 3/0482* (2013.01)
*G06F 16/587* (2019.01)

(52) U.S. Cl.
CPC .......... *G06F 3/0482* (2013.01); *G06F 16/587* (2019.01); *G16H 30/20* (2018.01)

(58) Field of Classification Search
CPC ....... G16H 30/20; G06F 16/58; G06F 16/587; G06F 3/0482
See application file for complete search history.

(56) References Cited

U.S. PATENT DOCUMENTS

| | | | | |
|---|---|---|---|---|
| 6,734,880 B2 * | 5/2004 | Chang | .................... | G16H 30/20 715/788 |
| 6,823,299 B1 * | 11/2004 | Contreras | ................. | G06F 8/24 703/27 |
| 8,046,044 B2 * | 10/2011 | Stazzone | ............ | G01R 33/4835 324/309 |
| 8,194,096 B2 * | 6/2012 | Hirakawa | .............. | G16H 30/20 345/670 |
| 8,867,807 B1 * | 10/2014 | Fram | ...................... | G16H 30/20 382/128 |
| 8,954,884 B1 * | 2/2015 | Barger | .................... | G06F 16/54 715/792 |
| 9,019,301 B2 * | 4/2015 | Matsue | .................. | G16H 50/20 600/407 |
| 9,081,876 B2 * | 7/2015 | Boccanfuso | ........... | G16H 30/40 |
| 9,177,110 B1 * | 11/2015 | Fram | ...................... | G06T 11/60 |
| 9,177,378 B2 * | 11/2015 | Schoenmeyer | ..... | G06F 3/04845 |
| 9,224,188 B2 * | 12/2015 | Li | ............................ | G06T 7/30 |
| 10,453,203 B2 * | 10/2019 | Kadir | ........................ | G06T 7/33 |
| 10,943,699 B2 * | 3/2021 | Li | ........................... | G06N 20/00 |
| 2005/0010606 A1 * | 1/2005 | Kaiser | ................. | G06F 16/2246 |

(Continued)

OTHER PUBLICATIONS

Murphy et al, "Cine imaging (MRI)," Aug. 3, 2020, Available http://web.archive.org/web/20200803205428/https://radiopaedia.org/articles/cine-imaging-mri?lang=us (Year: 2020).*

*Primary Examiner* — Alvin H Tan
(74) *Attorney, Agent, or Firm* — Kraguljac Law Group LLC

(57) ABSTRACT

Methods, systems, and computer-readable media are disclosed for organizing and linking image series for a patient in a linking graph. The organizing and linking of image series for a patient can be performed automatically and based on manual selection of a user. As a user scrolls through image instances of for a primary image series, image instances from linked image series that share position coordinates (or image instances closest thereto) are automatically and simultaneously presented to the user viewing the primary image series.

11 Claims, 16 Drawing Sheets

(56) References Cited

U.S. PATENT DOCUMENTS

| | | | |
|---|---|---|---|
| 2015/0088927 A1* | 3/2015 | Sarrazin | G06F 16/148 |
| | | | 707/769 |
| 2017/0039322 A1* | 2/2017 | Reicher | G06F 16/583 |

* cited by examiner

LINKING GRAPH

BACKGROUND

Digital Imaging and Communications in Medicine (DICOM) is used worldwide to store, exchange, and transmit medical objects/images. DICOM incorporates standards for imaging modalities such as radiography, ultrasonography, computed tomography (CT), magnetic resonance imaging (MRI), and radiation therapy.

A DICOM study is the imaging procedure (e.g., CT, MRI) being performed, at a certain date and time, at a healthcare facility on a patient. A single DICOM study often includes multiple series. A series may include the patient being physically scanned multiple times in one study (typical for MRI), or when a patient is scanned once and that data is reconstructed in different ways (typical for CT). Each physical scan or virtual reconstruction is considered a series. Each series may include multiple image instances. In one example, a full body CT study may include 100-500 series, where each series could have 6-20 image instances resulting in 2000-3000 images for a single CT study for a patient. An MRI study may include 30-40 series and also result in thousands of images. In addition, many patients have more than one study performed at different times during the course of diagnosis and treatment.

It can be difficult and time-consuming for a radiologist to view, organize, and compare thousands of image instances per patient per study in an effective manner to diagnose and treat a patient.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present disclosure is defined by the claims as supported by the Specification, including the Detailed Description.

Systems, methods, and storage media useful in a computing environment to organize and present images on a graphical user interface are provided. In one aspect, all of the image series from an image study of the same plane scroll together when one of the series is scrolled. A selection is received from a user to view a first image series. A first image instance from the first image series is displayed in an active viewport. A linking graph is accessed to determine linked images series linked to the selected first image series. The position coordinates of the first image instance are compared to the position coordinates of the linked image series to determine linked image instances that have the same position as the first image instance. The first image instance and the image instances from the linked image series that have the same position coordinates as the first image instance are automatically and simultaneously presented on a graphical user interface (GUI).

In additional aspects, as the user scrolls through the first image series, a selection from the user is received to view the first image series where a second image instance from the first image series is displayed in the active viewport. The position coordinates of the second image instance from the first image series are compared to the position coordinates of the linked image series to determine if linked image instances have the same position as the second image instance from the first series. The second image instance from the first image series and the image instances from the linked image series that have the same position coordinates as the second image instance are automatically and simultaneously presenting on a graphical user interface (GUI). When the image instance selected by the user is presented in the active viewport, the linking graph is navigated and the image instances from linked series with the same position coordinates as the image instance in the active viewport scroll and are presented in non-active viewports.

Systems, methods, and storage media useful in a computing environment to organize and present images on a graphical user interface are provided. A selection is received from a user to view a first image series. A first image instance from the first image series is displayed in an active viewport. A linking graph is accessed to determine linked images series linked to the selected first image series. The position coordinates of the first image instance are compared to the position coordinates of the linked image series to determine linked image instances that are the closest to the position coordinates of the first image instance from the first series. The first image instance and the image instances from the linked image series that are the closest to the position coordinates of the first image instance from the first series are automatically and simultaneously presented on a GUI.

In additional aspects, a selection from the user is received to view the first image series where a second image instance from the first image series is displayed in the active viewport. The position coordinates of the second image instance from the first image series are compared to the position coordinates of the linked image series to determine linked image instances to that are the closest to the position coordinates of the second image instance from the first series. The second image instance from the first image series and the image instances from the linked image series that are the closest to the position coordinates of the second image instance are automatically and simultaneously presented on a GUI to the user.

BRIEF DESCRIPTION OF THE DRAWINGS

Illustrative aspects of the present invention are described in detail below with reference to the attached drawing figures, and wherein.

DETAILED DESCRIPTION

Figure 1:
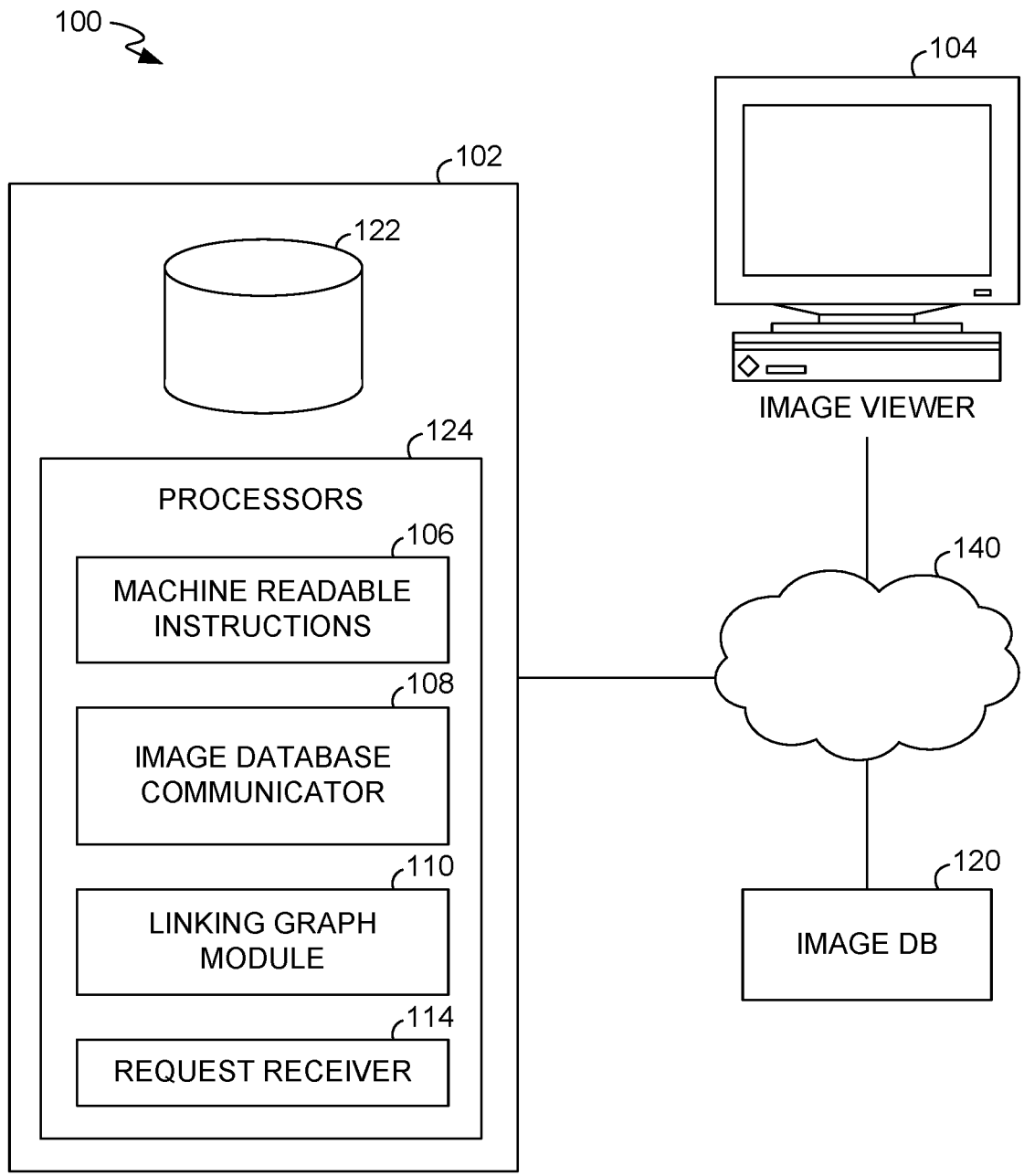
FIG. 1 illustrates a computing system, in accordance with aspects of the invention.

The subject matter of the present invention is being described with specificity herein to meet statutory requirements. However, the description itself is not intended to limit the scope of this patent. Rather, the inventors have contemplated that the claimed subject matter might also be embodied in other ways, to include different operators or combinations of operators similar to the ones described in this document, in conjunction with other present or future technologies. Terms should not be interpreted as implying any particular order among or between various operators herein disclosed unless and except when the order of individual operators is explicitly described. As such, although the terms "operator" and/or "block" can be used herein to connote different elements of system and/or methods, the terms should not be interpreted as implying any particular order and/or dependencies among or between various components and/or operators herein disclosed unless and except when the order of individual operators is explicitly described. The present disclosure will now be described more fully herein with reference to the accompanying drawings, which may not be drawn to scale and which are not to be construed as limiting. Indeed, the present invention can be embodied in many different forms and should not be construed as limited to the aspects set forth herein. Further, it will be apparent from this Detailed Description that the technological solutions disclosed herein are only a portion of those provided by the present invention. As such, the technological problems, solutions, advances, and improvements expressly referenced and explained herein should not be construed in a way that would limit the benefits, improvements, and/or practical application of the discussed aspects of the present invention.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media, as discussed further with respect to FIG. 1.

Embodiments herein provide a technological solution that addresses, solves, and overcomes the technological problems and/or shortcomings found in systems for presenting medical images to a user, such as a radiologist. Aspects of the invention improve existing solutions in that a linking graph allows tens, if not hundreds, of medical image series to be linked together. The linking graph supports both 1) auto synchronization of image series and 2) manual, radiologist-selected, image series to be linked. The linking graph allows for large amounts of data to be quickly displayed. For example, because a linking graph is traversed, several gigabytes of data may be displayed and images scrolled through with no downtime and does not cause a feedback loop like previous solutions utilizing linked lists in a relational database.

In computing, a linking graph is a database that uses graph structures for semantic queries with nodes, edges, and properties to represent and store data. A key concept of the system is the graph. The graph relates the data items in the store to a collection of nodes and edges, the edges representing the relationships between the nodes. The relationships allow data in the store to be linked together directly and, in many cases, retrieved with one operation.

Previous solutions for connecting images were performed in relational databases. Relational databases are unable to support both auto linked and manually linked image series and it is difficult to add and remove image series. Manual links in a relationship database exhibit non-deterministic or undesired behavior. Linked lists of images in a relational database are unable to quickly traverse several gigabytes of data and provide images scrolled through with no downtime. In addition, linked lists in relational databases are prone to getting stuck in a feedback loop.

Linking images in a linking graph, as described in aspects of the invention, provides the magnitude and direction of relationships between two or more image series (nodes) in a meaningful way. The linking graph is dynamic and makes it simple to add and remove linked image series both manually and using auto synchronization. The computer system utilizing the linking graph to link and present image series can quickly traverse gigabytes of data and more quickly process and present images to a user. The ability to quickly process and present images to a user allows a user to view multiple linked image series at time. For example, if a user is utilizing two to four monitors with four image series per screen, the user can evaluate sixteen to twenty linked image series at a time. A linking graph utilizes less power and memory than a relationship database and allows a user to view numerous linked image series at a time allowing the user to compare more tissue types to diagnose and treat a patient.

Aspects of the invention provide that when the user is scrolling through medical images instances from an images series in an active viewport of the image viewer, image instances linked by linking graph of the same plane and coordinates scroll together simultaneously with the image instances of the image series in the active viewport. Thus, all of the image series from an image study of the same plane scroll together when one of the series is scrolled. Thus, a user may directly compare images instances of the same plane and coordinates to see different tissue features.

Turning to FIG. 1, an exemplary computing system 100 is depicted. The computing system 100 (hereinafter "system") is merely an example of one suitable computing system and is not intended to suggest any limitation as to the scope of use or functionality of embodiments of the present invention. Neither should the system 100 be interpreted as having any dependency or requirement related to any single component or combination of components illustrated herein.

In some embodiments, one or more of the illustrated components may be implemented as a stand-alone application. The components described are exemplary in nature and in number and should not be construed as limiting. Any number of components may be employed to achieve the desired functionality within the scope of the embodiments hereof. Further, components may be located on any number of servers.

In the embodiment shown in FIG. 1, the system 100 includes an image manager 102, image instance database 120, network 140, and image viewer 104. Image viewer 104 is utilized by a radiologist to view medical images from various radiological exams. The image viewer 104 launches the actual medical image. As will be discussed herein, a radiologist will launch the image viewer 104, which may be configured to communicate with the image manager 102 and image instance database 120 to transmit the medical images from radiological exams to the image viewer 104. The image viewer 104 may be located on any user device, such as a laptop. Image view 104 typically includes an active viewport and several non-active viewports.

Image instance database 120 includes Digital Imaging and Communications in Medicine (DICOM) database. DICOM is used worldwide to store, exchange, and transmit medical images. DICOM incorporates standards for imaging modalities such as radiography, ultrasonography, CT, MRI, and radiation therapy.

A DICOM study is the imaging procedure (e.g., CT, MRI) being performed at a healthcare facility, at a certain date and time on a patient. The patient is the person receiving the imaging procedure. A DICOM study typically includes multiple image series. An image series can be a collection of DICOM images. An image series may include the patient being physically scanned multiple times in one study (typical for MRI), or when a patient is scanned once and that data is reconstructed in different ways (typical for CT).

Each image series may include multiple image instances. Each separate image instance may be a slice of a 3-D image or object. In this context, image instance data refers to the DICOM file. The DICOM file may include pixel data (image), instance number, series unique identifier (UID), study instance UID, patient identification (ID), patient's name, series description, and study description. In addition, from the pixel data, the image position coordinates specifying the x, y, and z coordinates, image orientation, and row and column value of the x, y, and z axes. The image position coordinates may specify the x, y, and z coordinates and the center of the first voxel transmitted. Image orientation specifies the direction cosines of the first row and the first column with respect to the patient. These position coordinates are provided as a pair with row value for the x, y, and z axes respectively followed by the column value for the x, y, and z axes respectively.

Figure 5:
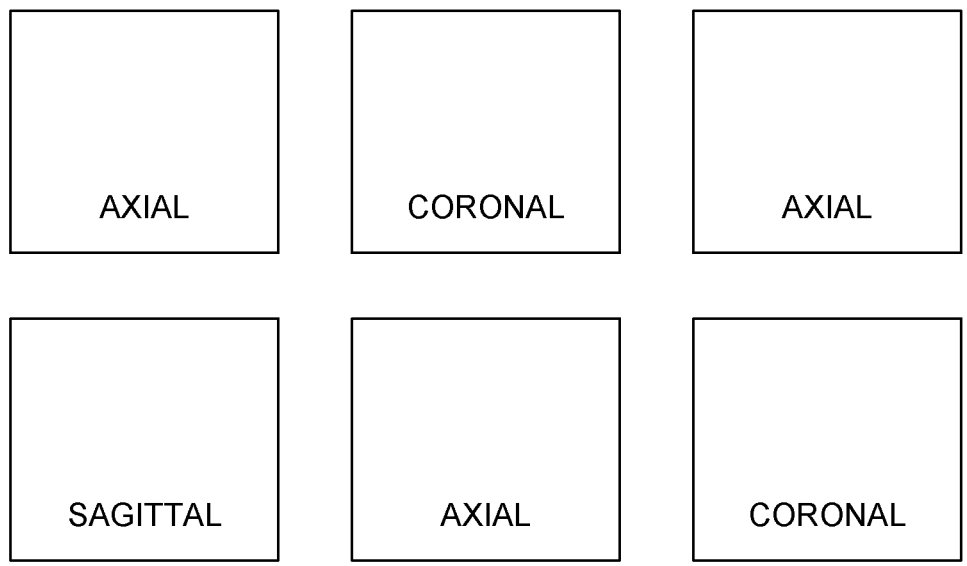
FIG. 5 depicts a graph of image instance series, in accordance with aspects of the invention.

With reference to FIG. 5, exemplary image series of an imaging study are depicted. The image series are grouped by axial, coronal, or sagittal anatomy planes. This example has three axial image series, two coronal image series and one sagittal series. These six series are from the same study (e.g., MRI). All of these series from the same study were captured at the same time and share the same DICOM frame of reference UID. The three axial image series are parallel and were captured at a different gradient. Each series in this example includes separate image instances. However, it will be appreciated that any number of magnetic values, filters, or contrasts may be utilized to capture images and a series may have any number of image instances.

Generally, the image manager 102 is configured to link and organize medical image series and instances provided by image instance database 120 to be displayed by image viewer 104 to a radiologist. In this embodiment, the image manager 102 is comprised of machine readable instructions 106, image database communicator 108, linking graph module 110, and a request receiver 114. It will be appreciated that any variety of programming languages can be used for image manager 102 including, but not limited to, Javascript. The image manager 102 may be comprised of more or fewer modules and any and all variations are contemplated herein. The components described are exemplary in nature and in number and should not be construed as limited. Any number of components may be employed to achieve the desired functionality within the scope of the embodiments hereof.

Additionally, in some aspects, the image manager 102 may also be located within the image instance database 120. It will be appreciated that some or all of the subcomponents of the image manager 102 may be accessed via the network 140 and may reside on one or more devices. Further, while system 100 is comprised of one image manager 102, it is contemplated that the system 100 may include more than one image manager 102. It is also contemplated that the image manager may be integrated into the image viewer 104.

The image database communicator 108 within the image manager 102 is configured to receive an image instance data from image instance database 120. The request receiver 114 receives a request from the user to view one or more medical image series. When a user, such as a radiologist, either at a facility or remotely, needs to view medical image series from radiological exams, the radiologist may launch the image viewer 104 and select an image series to view in the active viewport of image viewer 104. The image series may be pre-loaded in the image viewer 104 or may be sent over by the image instance database 120 as requested. User selection of the image series to view in the active viewport of image view 104 is transmitted to image manager 102 and received by request receiver 114. Additionally, the request received by the request receiver 114 may also comprise an order number that is associated with the radiological exam and medical image series to be viewed.

Figure 18:
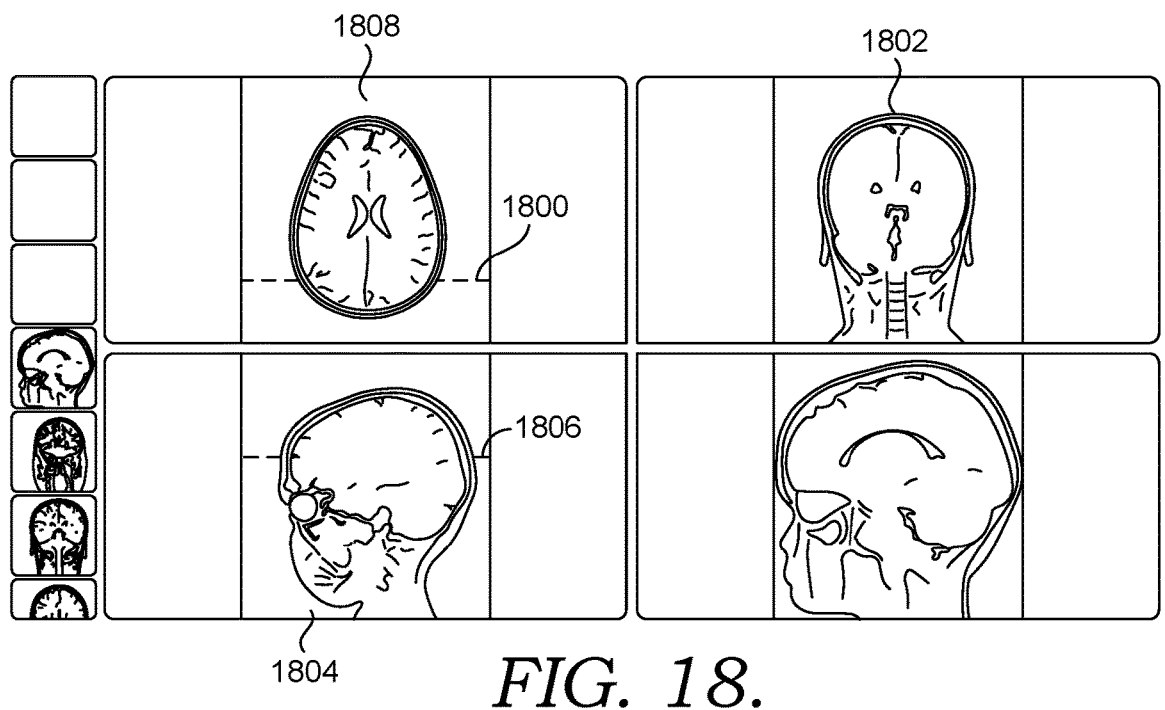
FIG. 18 depicts exemplary axial, coronal and sagittal images.

Next, the linking graph module 110 identifies one or more images series linked to the image series requested to be viewed by the user. Linking graph module 110 allows for multiple images series to be linked and displayed automatically and simultaneously. This is an improvement to existing technology and removes the previous restrictions of prior systems. While more than one image could previously be viewed, the images were not organized by linking graphs according to coordinates and/or closeness. Linking graphs minimizes the computation power needed and prevents feedback loops. For example, while the image viewer 104 previously may have allowed a user to view different images simultaneously as shown in FIG. 18. For example, FIG. 18 depicts a reference line 1800 on axial plane image 1808 show where the coronal plane image 1802 was taken and reference line 1806 of sagittal plane image 1804 shows where coronal plane image 1802 was taken.

Figure 2:
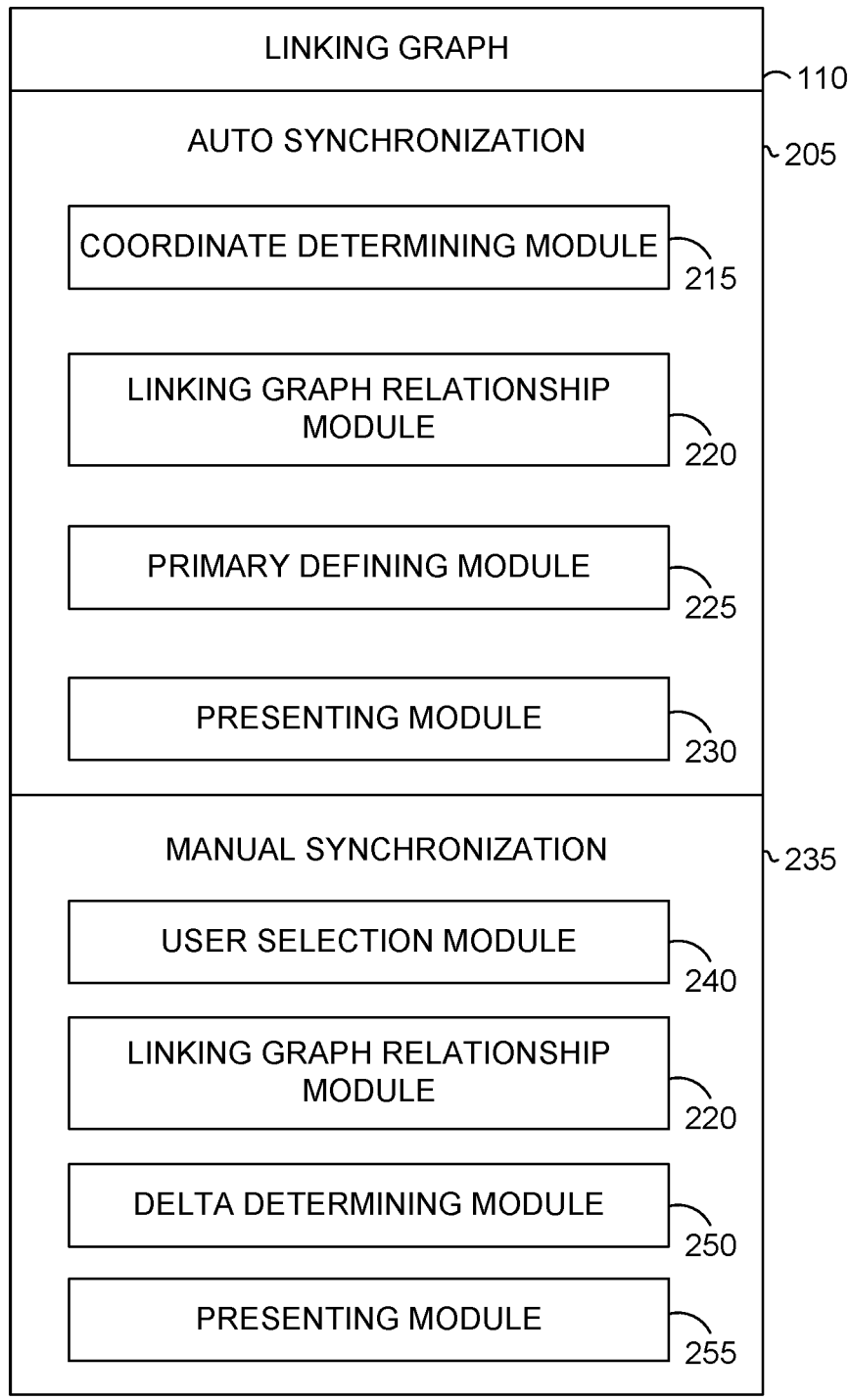
FIG. 2 depicts a linking graph module, in accordance with aspects of the invention.

For aspects of this invention, when the request receiver 114 receives the request to view an image series, the linking graph module 110 identifies image series linked to the selected image series that have been synchronized automatically or manually. As can be seen in FIG. 2, linking graph module 110 includes both auto synchronization module 205 for synchronizing images from different series within a single study and manual synchronization 235 for synchronizing images from different studies.

Auto synchronization module 205 includes coordinate determining module 215, linking graph relationship module 220, primary defining module 225, and presenting module 230.

Figure 6:
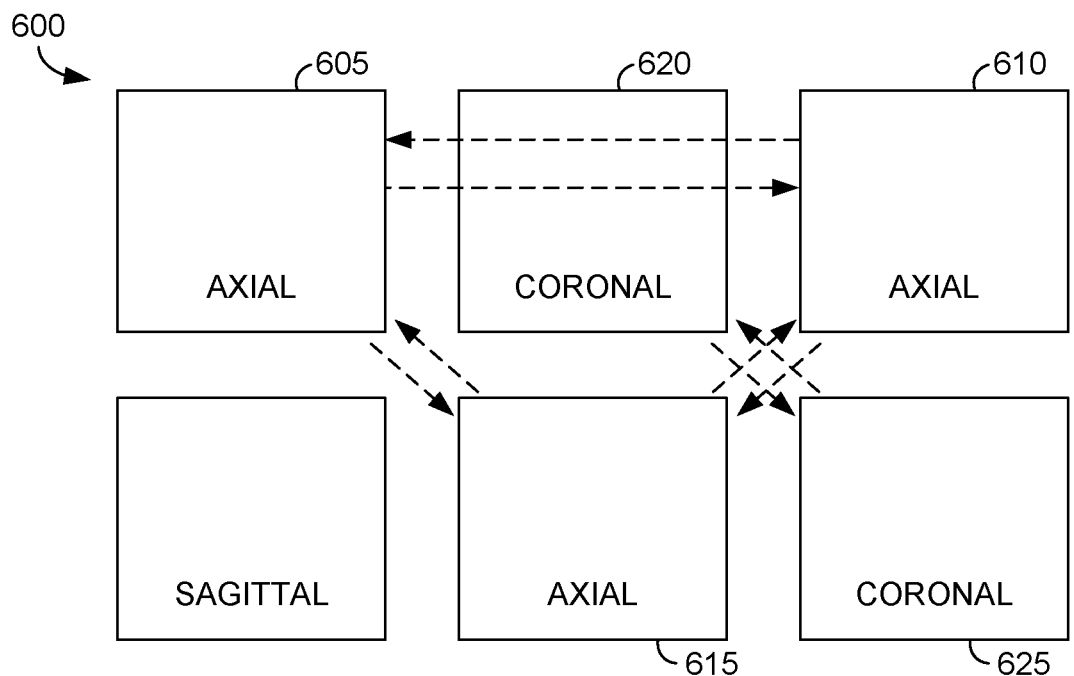
FIG. 6 depicts a linking graph of image instance series from an image study, in accordance with aspects of the invention.

Linking graphs are generally comprised of static data that is then to be queried/analyzed and subsequently displayed to the user. Linking graph relationship module 220 provides that a disparate image series for a patient from an image instance database 120 can be displayed as nodes within linking graphs and the links between them as edges within that graph. Linking graphs show the magnitude and direction of relationships between two or more nodes (image series). Linking graphs can be used in link analysis for identifying relationships between nodes that are not easy to see from the raw data. FIG. 6 depicts an exemplary linking graph 600 having different axial series 605, 610, and 615 from the same study for a patient linked by linking graph relationship module 220. In addition, the different coronal series 620 and 625 from the same study are linked by linking graph relationship module 220.

Linking graph relationship module 220 links image series shown in linking graph of FIG. 6. The linking graph relationship module 220 depicts the different series of the study as a bi-directional graph. The dashed arrows represent an automatic link from one series to a different image series (nodes) in the study for a patient. In FIG. 6, all three of the axial series of the study are related to one another and the two coronal series of the study are linked to one another. The different image series with the same plane automatically linked together and the relationships are stored by linking graph relationship module 220. The linking graph is dynamic in memory that changes as the user displays more or different automatically linked image series and creates/destroys links between them. The linking graph relationship module 220 is utilized to the user interface relationships of viewports within the image viewer 104.

Figure 7:
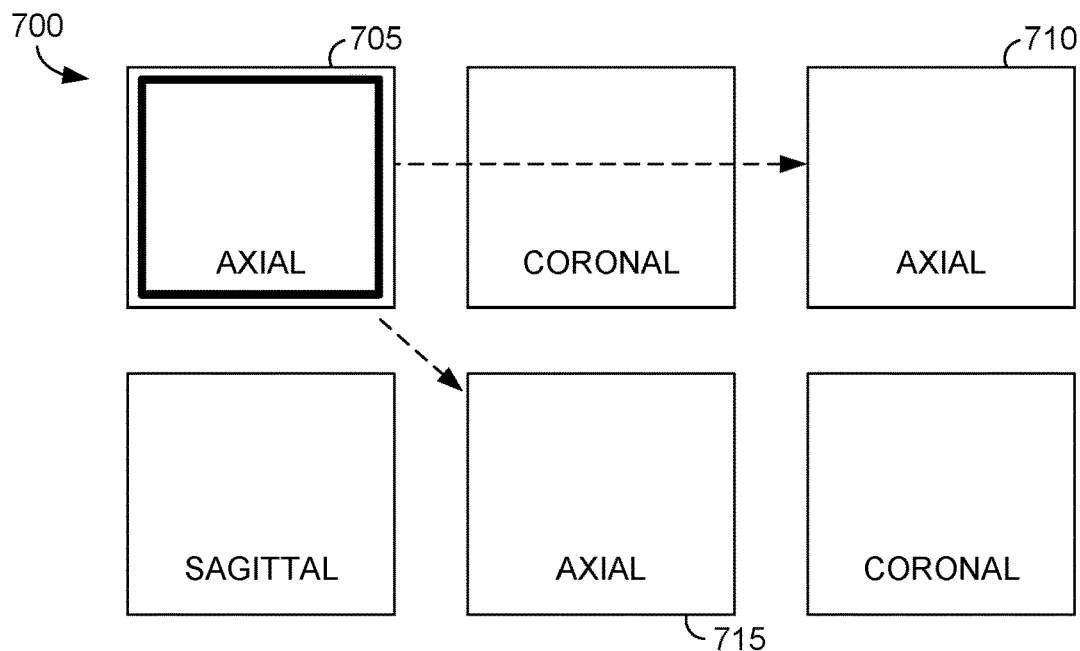
FIG. 7 depicts an active viewport for a linking graph, in accordance with aspects of the invention.

Primary defining module 225 determines the primary image series by which the linked images will be determined to display to the user. With reference to FIG. 7, the user is viewing an image in the active viewport 705. In this instance, the upper left axial image series is considered the primary or root image series 705 of the linking graph as it is the series is being viewed by the user in active viewport. Image series 710 and 715 are linked to series 705 by linking graph relationship module 220. Thus, when a user navigates through the upper left axial image series 705 in the active viewport, the axial series 710 and 715 to align themselves with the upper left axial image series 705 based on an attribute of the edge.

For automatic synchronization, the attribute of the edge implies that the alignment occurs based on the image position (or closest thereto) in physical space coordinates in the imaging coordinate system by coordinate determining module 215. Coordinate determining module 215 of auto synchronization module 205 determines images from linked image series that have the same plane from linking graph relationship module 220 and compares the location coordinates of image instances of the linked image series to the location coordinates of the image instance of the primary image series being viewed in the active viewport. For example, in FIG. 7 coordinate determining module 215 determines from linking graph relationship module 220 that image series 705, 710, and 715 are the same plane (axial) and a linked from the same study. For example, axial series 705, 710, and 715 are from the same MRI study image instances captured on the same plane with the same location coordinates but using different filters or gradients.

When a first image from a first series 705 is shown in the active top left viewport, the graph 700 of FIG. 7 is traversed by linking graph relationship module 220 to the second and third series nodes 710 and 715. The coordinate determining module 215 accesses the image instances for the second and third series nodes to find image instances that correspond to the image position and have the same or closest position coordinates to the first active image from the first series in the viewport. It will be appreciated that coordinate determining module 215 determines the image instances that have the same coordinates and location as the first active image from the first series in the viewport or the image instance for each series that is the closest in position coordinates.

Coordinate determining module 215 of auto synchronization module 205 determines images from the image series having the same plane and image instance coordinates from different series within a study. For example in FIG. 6, coordinate determining module 215 determines the image instances from axial series from a single study. For example, in an MRI study, there may be a number of series having of image instances captured on the same plane with the same coordinates but using different filters or gradients. These image instances from different series with the same plane and same coordinates may be automatically linked together by linking graph relationship module 220.

Presenting module 230 presents the automatically linked images instances in image viewer 104 from the second and third series 710 and 715 that correspond to position of the automatically linked image instance from the first series 705 being viewed in the active viewport. For example, when determined from linking graph relationship module 220 the second and third series images instances that correspond to the position coordinates are displayed in non-active viewports in image view 104 by presenting module 230.

Figure 19:
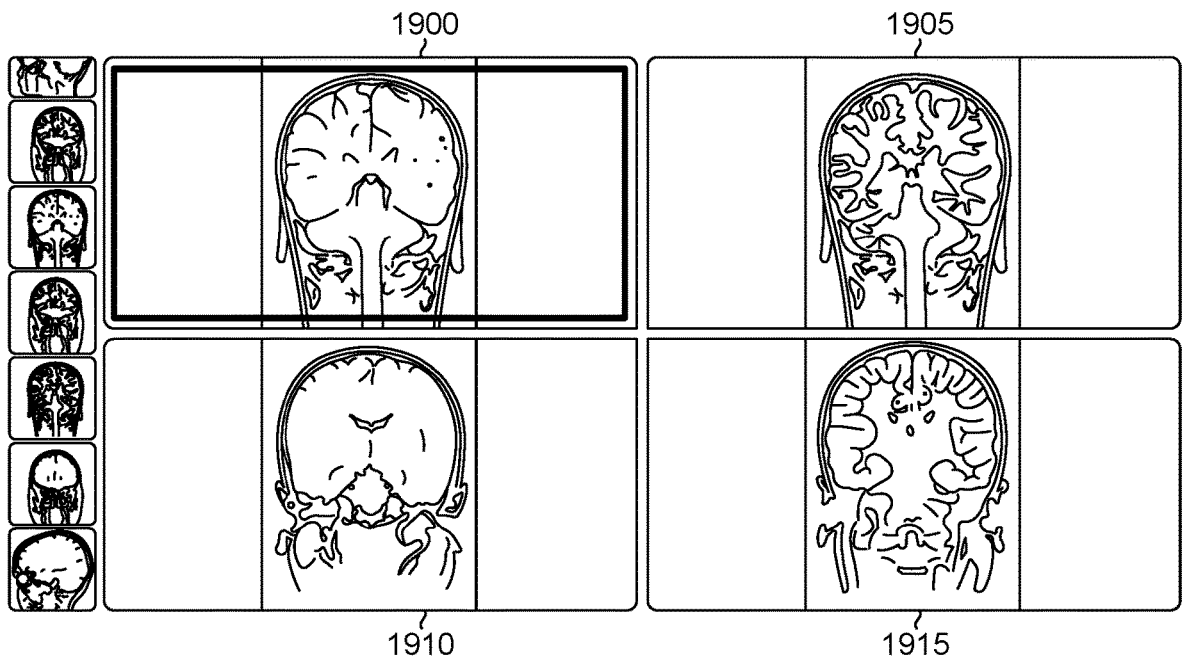
FIG. 19 depicts a graphical user interface having an active viewport and auto synchronization of images, in accordance with aspects of the invention.

The user selected medical image instance is shown in the active viewport and the linked images instances are shown in the non-active viewports. For example, with reference to FIG. 19, the user selected medical image instance from the active series is displayed in the upper left active viewport 1900 and the linked images are displayed in the upper right, lower right, and lower left viewports 1905, 1910, and 1915. When the user is scrolling medical images instances from the active images series in the image viewer 104, the images instances linked by same plane and coordinates scroll together simultaneously with the image instances of the active image series. Thus, a user may directly compare images instances of the same plane and coordinates to see different tissue features.

Figure 8:
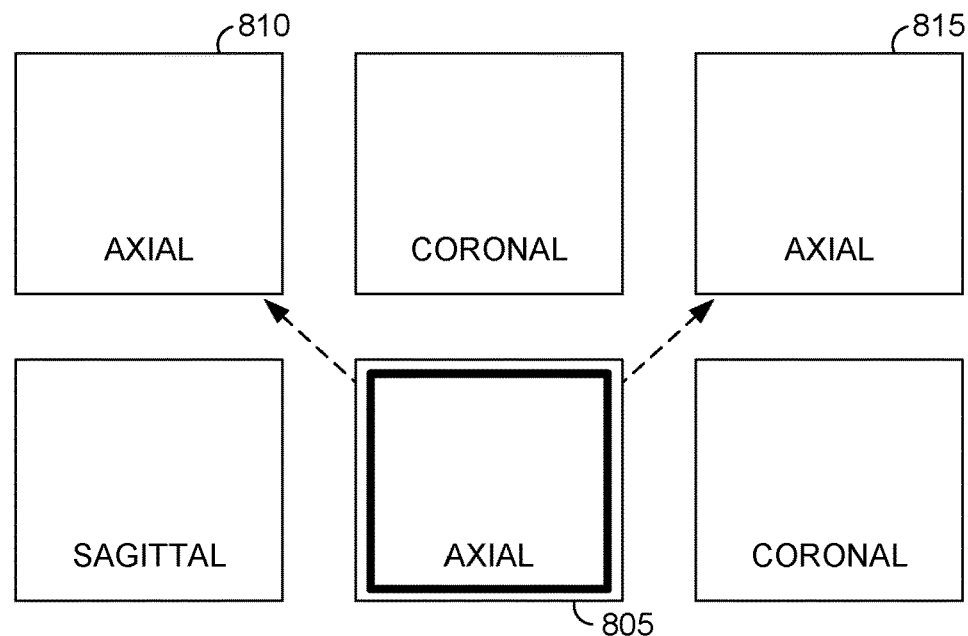
FIG. 8 depicts a change in active viewport for a linking graph, in accordance with aspects of the invention.

It will be appreciated that the user can change the active viewport to a different image and image series making the new images series the primary or root image series. For example, with reference to FIG. 8, the lower middle axial image series 805 becomes the activated viewport by the user and becomes the primary image series. The linking graph module 110 traverses the other series of images based on the new primary images series and updates the viewports 810 and 815 with images that correspond to the image instance position of the new primary image series.

Figure 9:
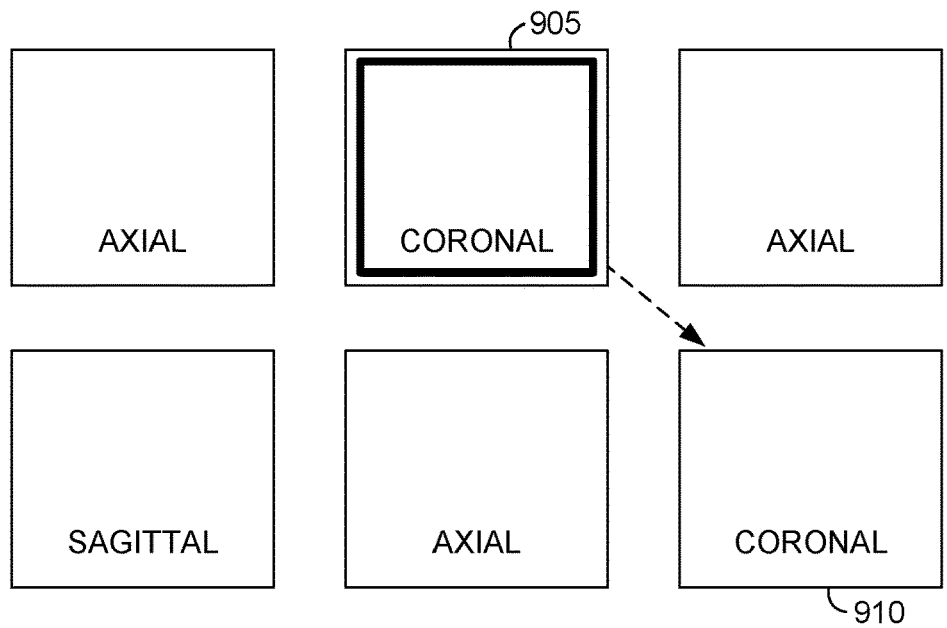
FIG. 9 depicts a change in plane and active viewport for a linking graph, in accordance with aspects of the invention.

It will also be appreciated that the user can change the active viewport to a different image plane image series as shown in FIG. 9. In this example, the coronal image plan series in the upper middle 905 of the graph is activated and becomes the primary image series. The linking graph module 110 traverses the linked coronal series 910 based on the new primary image series and updates the view 910 with a coronal image that corresponds to the image instance position of the new primary coronal image series.

Figure 20:
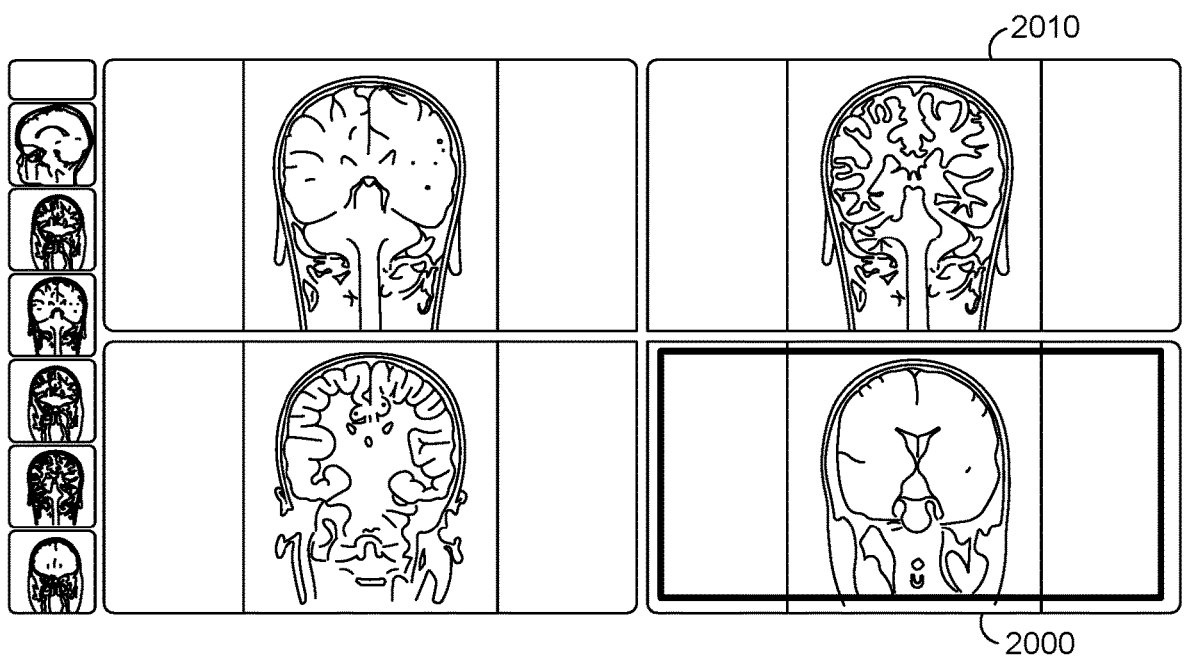
FIG. 20 depicts a graphical user interface for manual synchronization of image instance series, in accordance with aspects of the invention.

Manual synchronization module 235 includes user selection module 240, linking graph relationship module 220, delta determining module 250 and presenting module 255. Manual synchronization 235 links image series that have been manually selected by a user. User selection module 240 permits a user, such as a radiologist, to select two or more image series to link together. For example, when viewing images from a CT study 2000 for the patient as shown in FIG. 20, a user may choose to link images from an earlier CT study 2010 for the same patient. Manual synchronization can be done at a study or series level.

Figure 10:
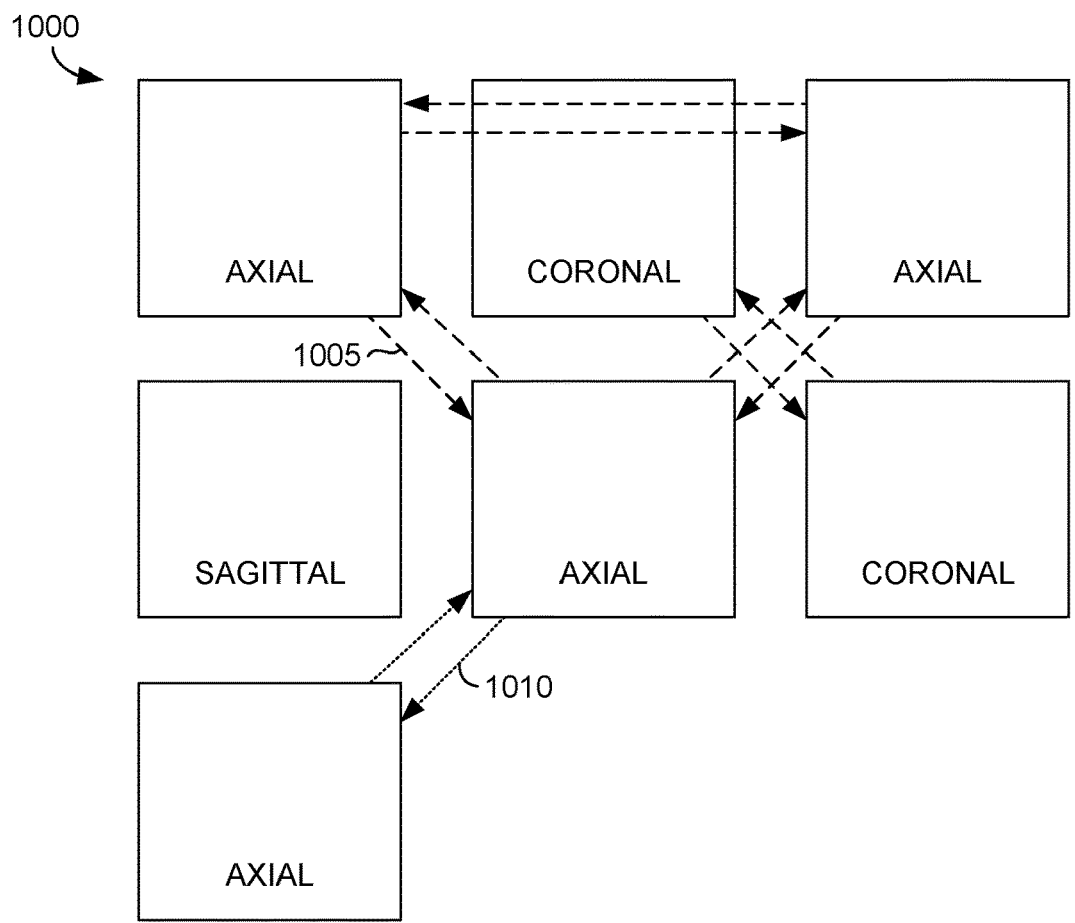
FIG. 10 depicts manual synchronization of image instances in a linking graph, in accordance with aspects of the invention.

Linking graph relationship module 220 stores the relationship between the two or more image series. With reference to FIG. 10, by using a graph 1000 for the dynamic tracking of linked image series, manual links 1010 are chained together along with automatic links 1005. In this example, the three axials of a procedure are automatically (dashed lines 1005) linked together but a fourth axial from a different frame of reference is manually linked (dotted lines 1010) by the user.

Figure 11:
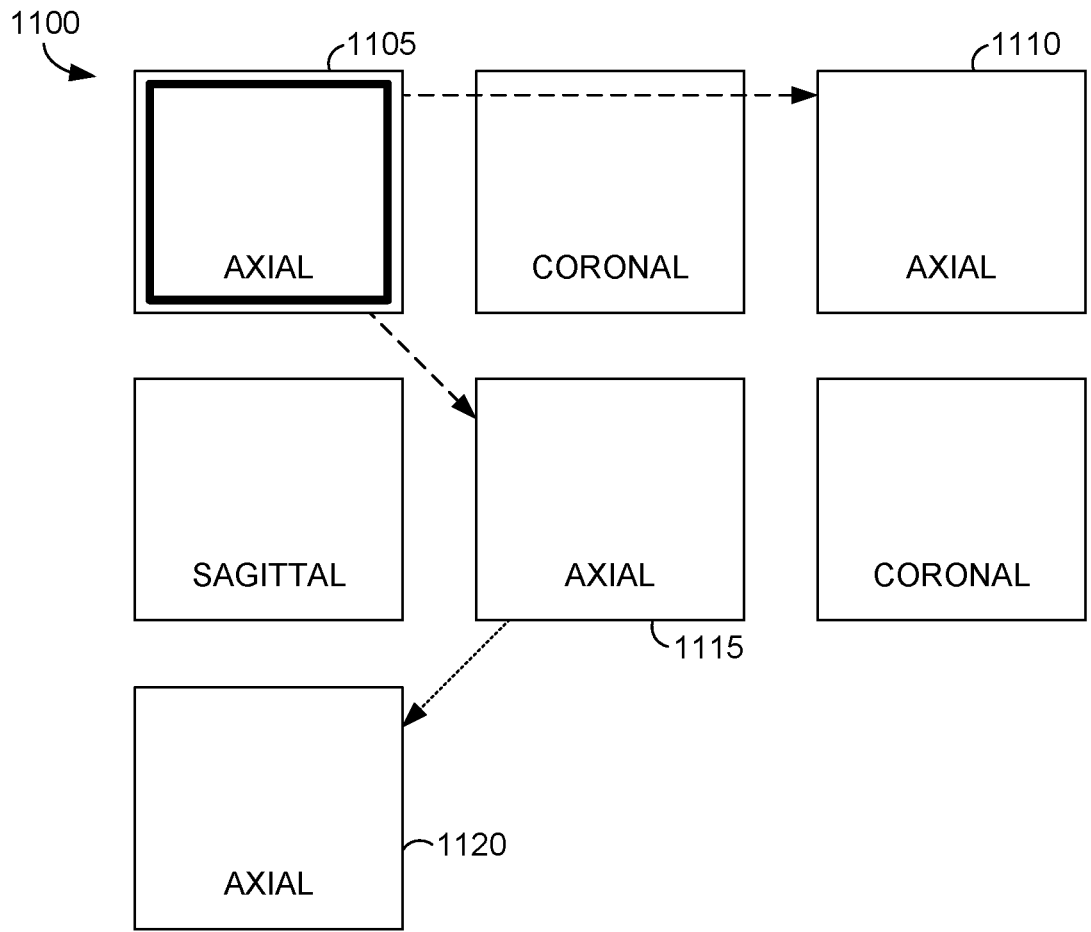
FIG. 11 depicts an active viewport for a linking graph, in accordance with aspects of the invention.

With reference to FIG. 11, in linking graph 1100, the top left axial image series 1105 is the active viewport and it aligns the axial image series 1110 and 1115 as those were auto synced with top left axial image series 1105 of that study. As axial series 1120 was manually linked to axial series 1115, this creates an indirect linking relationship with top left axial image series 1105 and indirectly causes the alignment of the fourth axial image series 1120.

With reference to FIG. 11, the top left axial series 1105 is the primary viewport. The path from the top left axial series 1105 to the lower left axial 1120 is calculated by 1) determining the path from top left axial series 1105 to the middle axial 1115 and 2) the path from the middle axial 1115 to the lower left axial 1120. The path from the top left axial series 1105 to the lower left axial series 1120 is determined based on auto syncing of the series and the expected change between in the physical space coordinates. The top left axial series 1105 causes the middle axial series 1115 to move to the exact same position (or closest thereto) in physical space coordinates. As such, an image instance of the top left axial series 1105 in the primary viewport has the same physical space coordinates as the middle axial image instance 1115 being viewed. As the image instances of the top left axial series 1105 are scrolled the instance images for the middle axial image instances 1115 are moved to the same position (or closest thereto) in physical space coordinates as the top left axial series 1105.

Next, the path from the middle axial series 1115 to the lower left axial series 1120 is determined based on the manual linking of the middle axial series to the lower left axial series. The path from the middle axial series 1115 to the lower left axial series 1120 is calculated by the delta determining module 250 with the delta of the offset or image position from the top left axial series 1105 aligned with the middle axial series 1115 (auto synchronized image). The delta triggers the distance of navigation in the lower left axial series (manual linked series) 1120 from the primary image series top left axial series 1105 (primary image series). For example, if image instances from series for 1105 and 1115 were offset 5 mm (delta) in image position, the image selected to be displayed for 1120 would be within 5 mm offset from the position (or closest thereto) of 1115.

Figure 12:
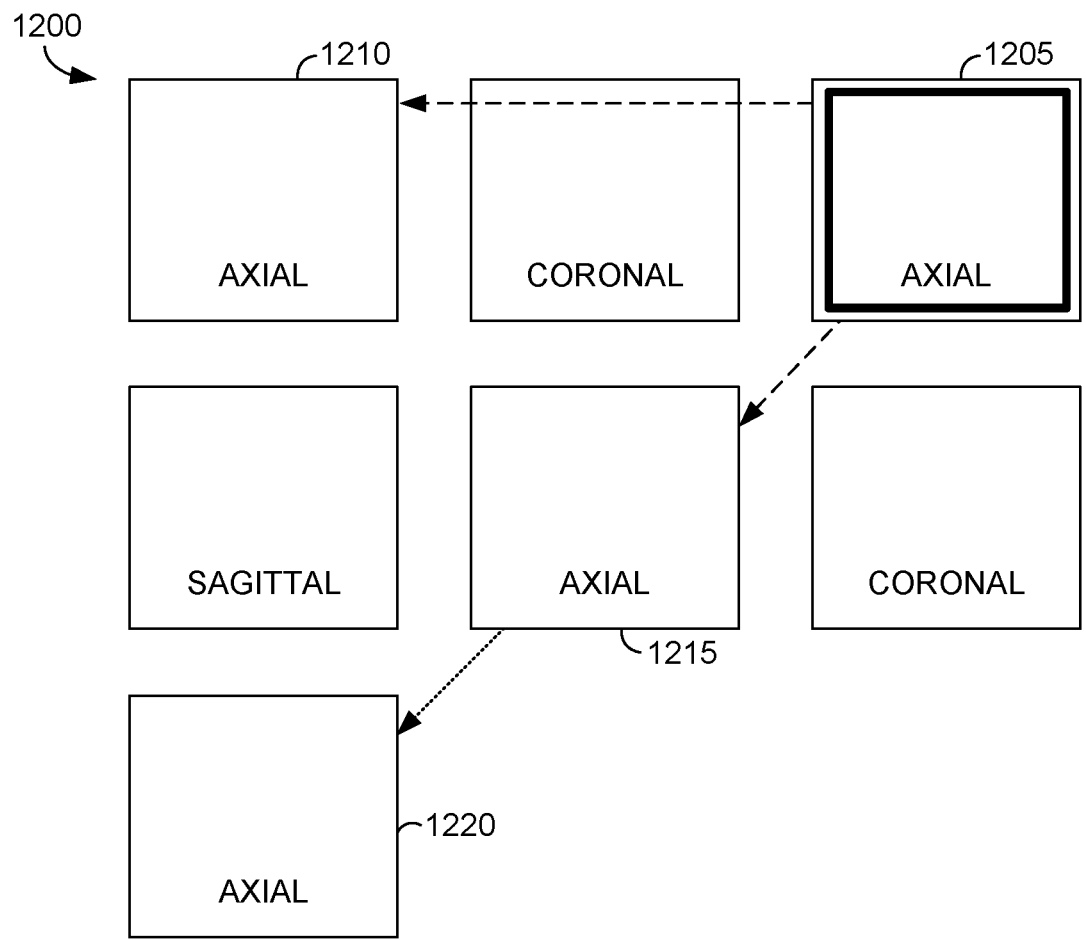
FIG. 12 depicts a change in active viewport for a linking graph, in accordance with aspects of the invention.

With reference to FIG. 12, in linking graph 1200, the top right axial image 1205 is the active viewport and it directly aligns with the axial image series 1210 and 1215 that were auto synced from the same study. As axial image series 1220 was manually linked to axial image series 1215, axial image series 1205 indirectly aligns with axial image series 1220.

Figure 13:
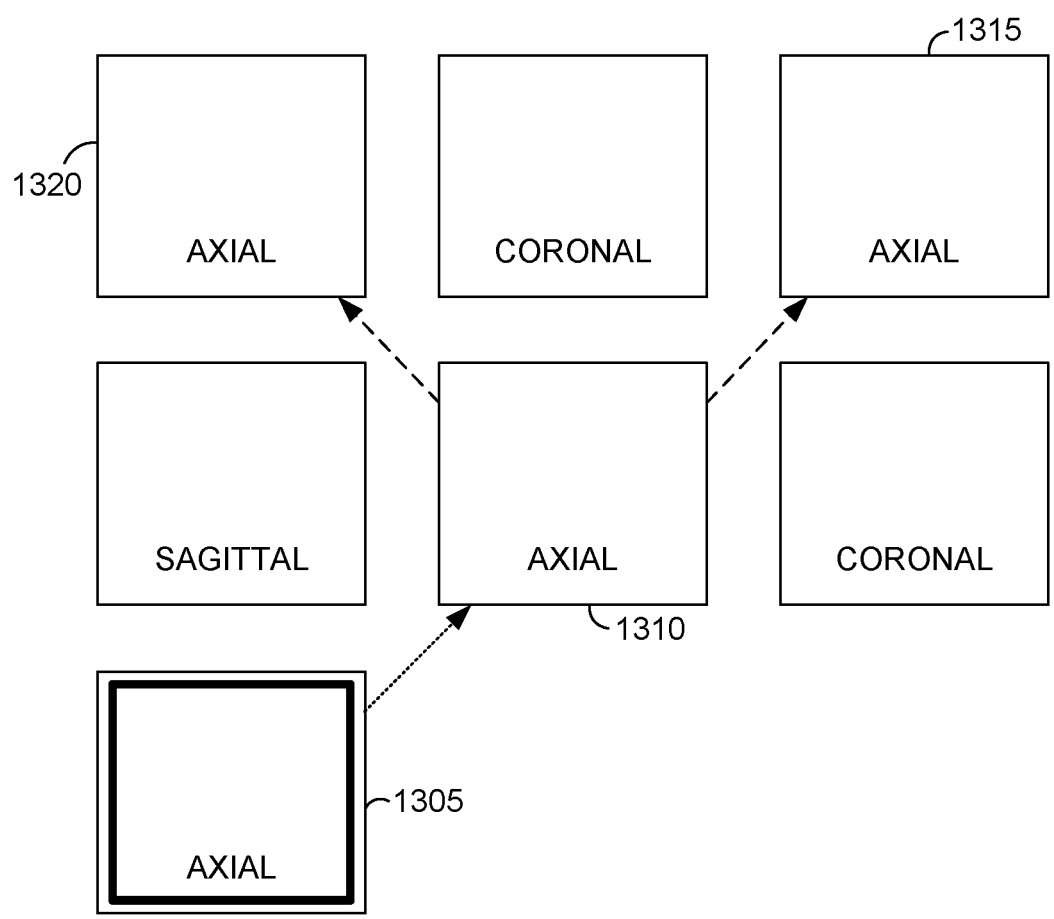
FIG. 13 depicts an active viewport for a linking graph, in accordance with aspects of the invention.

With reference to FIG. 13, a linking graph is shown when the lower left axial series 1305 is in the active viewport, it directly aligns with axial image series 1310 with which it is manually linked. As such, axial image series 1310 is indirectly linked with axial image series 1315 and 1320 which were auto synced with axial image series 1310.

Figure 14:
FIG. 14 depicts auto and manual synchronization of image instance series, in accordance with aspects of the invention.

With reference to FIG. 14, linking graph relationship module 220 traverses a linking graph to determine auto synchronized image series and manually synchronized image series. Linking graph relationship module 220 calculates paths between image series by length and process them from shortest to longest. Paths that are only of length 1 are processed first, then of length 2. By employing this strategy, all paths are processed incrementally such that when a path of length 3 is processed the edges from the first two segments of that path have already been processed and those series have already been aligned. Thus, when a path of length 3 is processed only the offset or position delta difference has to be calculated by delta determining module 250 for the last segment of the path and then applied to the end node.

In this manner, all secondary, tertiary, effects can be processed by simply iterating these paths and aligning the series accordingly and do not have to be reactive. This also means that even though auto and manual links may be chained together their compound effects only need to be calculated one segment at a time providing more efficiency as a user scrolls through images in the image view.

Figure 15:
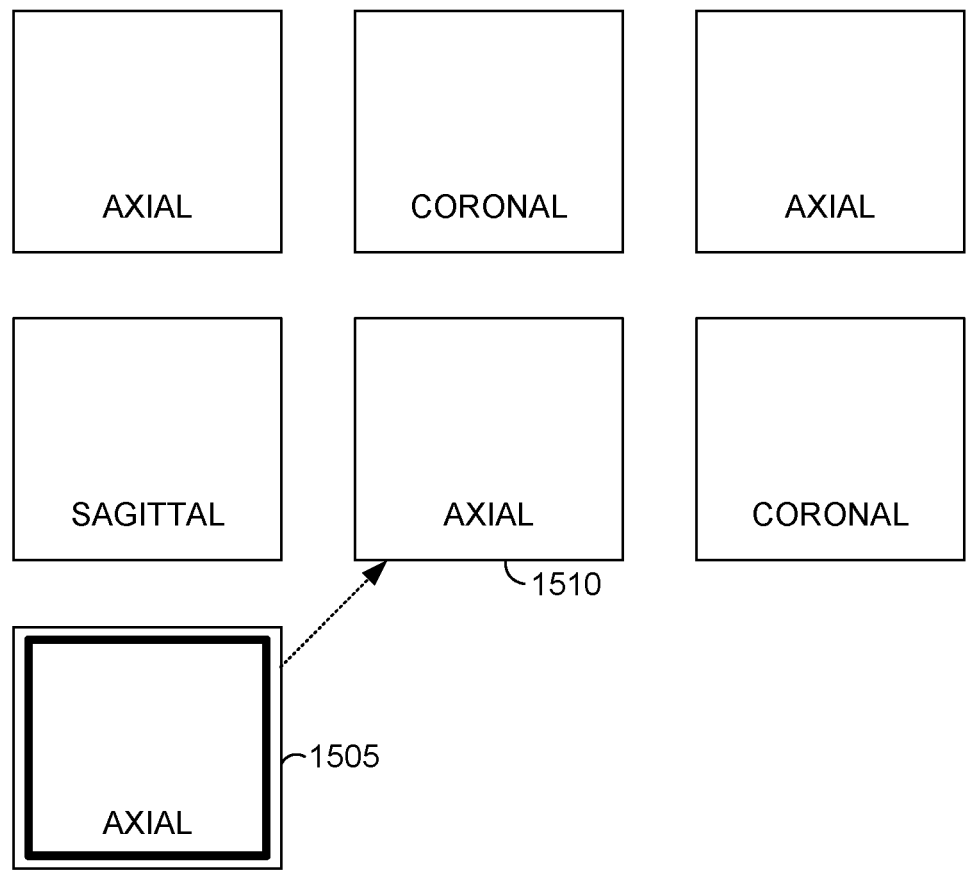
FIG. 15 depicts disabling auto synchronization of image instance series, in accordance with aspects of the invention.

In one aspect, linking graph relationship module 220, can disable the auto synchronization of images without rebuilding the linking graph. As shown in FIG. 15 when the auto synchronization links are disabled their edges are considered invalid, so the paths which contain them are not traversed and the lower left axial 1505 now only directly controls the alignment of the axial 1510 with which it is manually linked.

Figure 16:
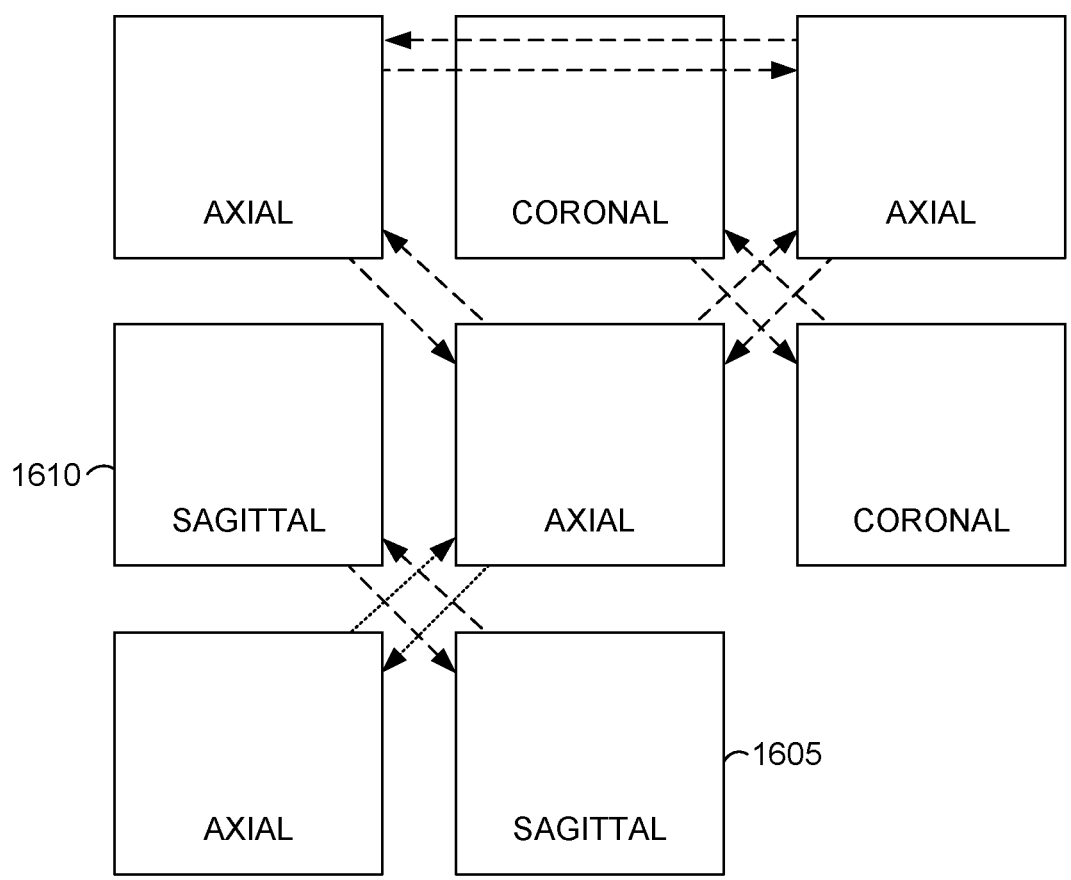
FIG. 16 depicts adding a series in a linking graph, in accordance with aspects of the invention.

In another aspect, linking graph relationship module 220, can add another series to the linking graph as shown in FIG. 16. When another series is added to the linking graph and it is a capture of a plane that is already displayed, auto synchronization links can be automatically established by adding a new node and re-merging all edges of the graph including any new edges. For example, when another sagittal view 1605 is added to the linking graph it can be automatically associated with the other sagittal view 1610 that is already part of the linking graph.

Figure 17:
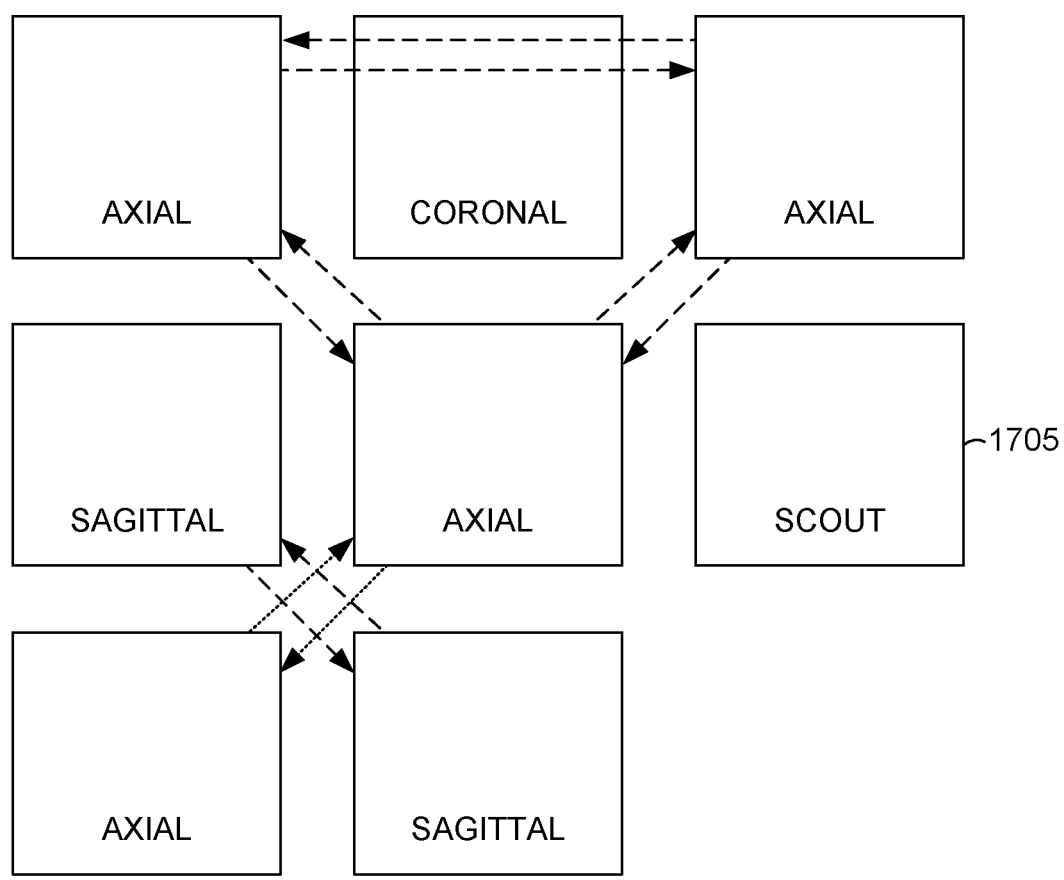
FIG. 17 depicts substituting a series in a linking graph, in accordance with aspects of the invention.

In another aspect, linking graph relationship module 220, can remove a series from the linking graph and/or replace it with a series of a different plane of capture. With reference to FIG. 17, the node simply has to be dropped from the graph and replaced. For example, this case the middle right coronal series was replaced with a scout image series 1705.

Figure 3:
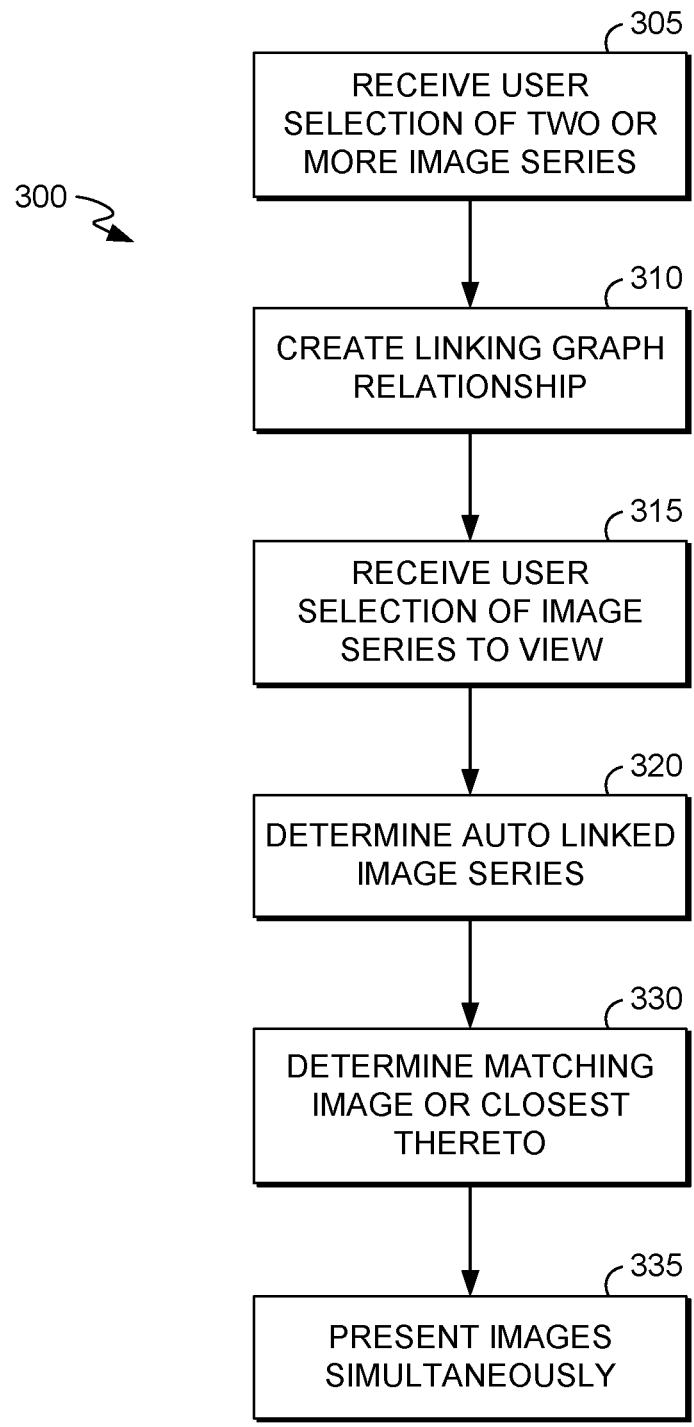
FIGS. 3 and 4 depict flow charts for generating and presenting linked images, in accordance with aspects of the invention.

Turning now to FIG. 3, a method 300 for creating manual linking graph relationships between multiple image series and presenting images to a user is provided.

At 305, user selection of two or more image series (or studies) to link together is received. At 310, a linking graph relationship is created. As can be seen in FIG. 13, there is a manual link between series 1305 and series 1310. User has selected the two series from image viewer 104 and indicated that the series are related. If auto synchronization is active, as shown in FIG. 13, series 1305 becomes linked to series 1320 and 1315 based on their auto synchronization relationship with series 1310. As mentioned above, by modeling the linking relationships as a graph, manual links can be chained to auto synchronized image series before or after auto synchronization.

At 315, user selection of image series to view in active viewport is received. Navigation is triggered for the active viewport. At 320, the linking graph is traversed for the image series that corresponds to the active viewport and image series linked to the active image series are then aligned accordingly. Images from the active series and the linked series may be aligned based on view position synchronization. View position auto synchronization can be enabled/disabled in tandem with auto synchronization and applies to computed radiography (CR), digital radiography (DR), digital X-Ray (DX), mammography (MG) modalities. At 330, when one of these image series is loaded, the DICOM View Position (0018,5101) attribute is read from the image and a matching image is attempted to be found within the linked image series. If an image instance is found in the linked series that has the same view position as this image in the active viewport, then at 335 this matching image is presented simultaneously with the image in the active viewport. If the linked image series does not have a matching image to the image in the active viewport, the closest linked image to the active image position is determined and displayed simultaneously with the active image at 335. For example, the delta between the active image position and the linked image position can be calculated. As the images are scrolled through, the linked image may be held until a new linked image is identified that has a smaller position delta that then current linked image and the current active image. It will be appreciated that the in some instances linked series are aligned based on view position synchronization with an exact position match to the image in the active view port or in some instances the image from the linked series that is closest to the image position in the active viewport.

Figure 4:
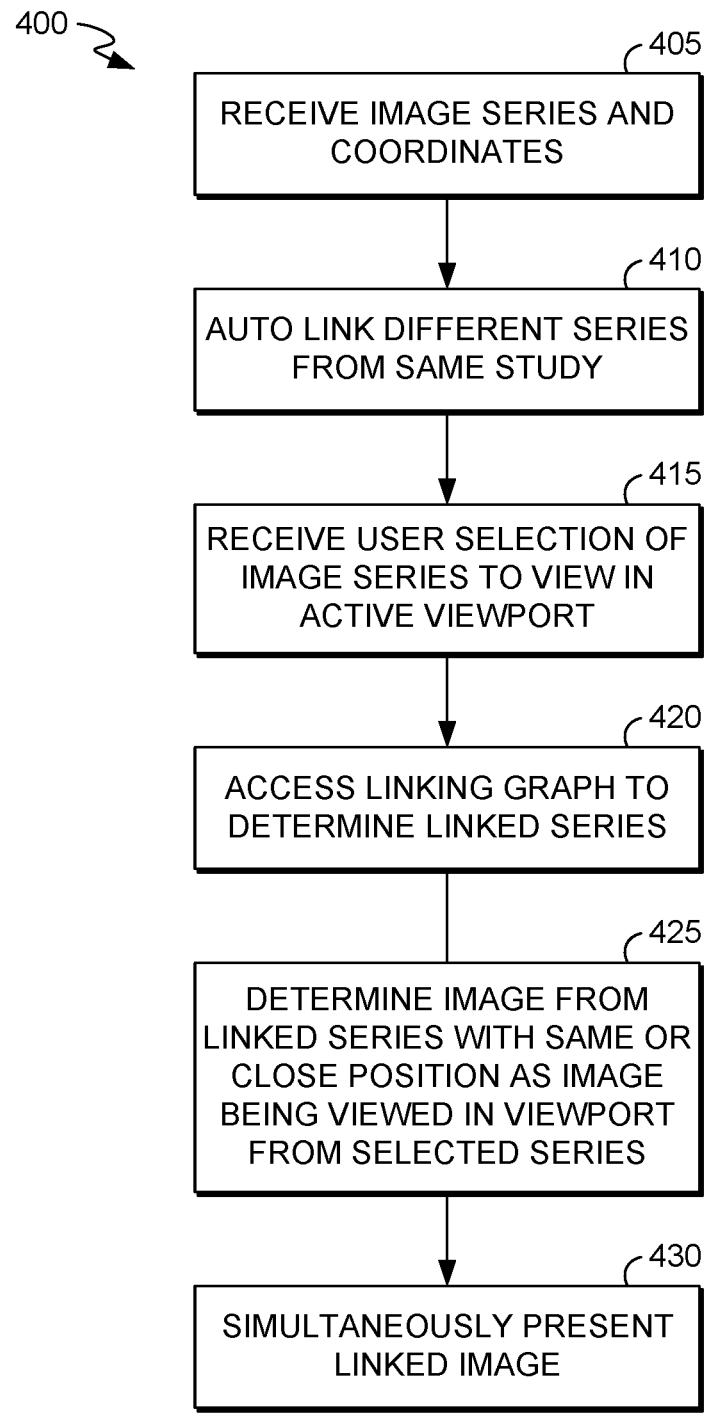

Turning now to FIG. 4, a method 400 for creating auto linking graph relationships between multiple image series and presenting images to a user is provided. At 405, image series data and coordinates are from a single image study for a patient. At 410, series from the same study are automatically linked together in a linking graph. Edges generated that correspond to auto-synchronization are created between image series that share the same DICOM frame of reference UID and have that as an attribute as well as the corresponding DICOM image plane module and a type attribute of auto synchronization. The type attribute allows edges to be filtered when auto synchronization is disabled.

At 415, user selection of image series to view in active viewport is received. Navigation is triggered for the active viewport. At 420, the linking graph is traversed for the image series that corresponds to the active viewport and image series linked to the active image series are then aligned accordingly. At 425, images from the active series and the linked series are aligned based on view position synchronization. When one of these image series is loaded, the DICOM View Position attribute is read from the image and a matching image with the same view position (or closest thereto) is attempted to be found within the linked image series. If an instance is found in a different series that has the same view position as this image in the active viewport, then this matching image is presented simultaneously with the image in the active viewport. The view position is a series level attribute that can be retrieved directly from the DICOM header. View positions will be considered a match if they are inverted (Posterior-Anterior vs Anterior-Posterior). It will be appreciated that in some instances linked series are aligned based on view position synchronization with an exact position match to the image in the active view port or in some instances the image from the linked series that is closest to the image position in the active viewport.

At 430, the matching or closest images from the linked image series are presented simultaneously with the primary image from the image series in the active viewport. If there is an active viewport and that viewport supports auto synchronization then the navigation will cause displayed image series align accordingly when presented to the user.

With reference to FIG. 1, image manager(s) 102 may be configured to communicate with one or more image viewers 104 according to a client/server architecture, a peer-to-peer architecture, and/or other architectures. Image viewer(s) 104 may be configured to communicate with other image viewers via image manager(s) 102 and/or according to a client/server architecture, a peer-to-peer architecture, and/or other architectures. Users may access system 100 via image viewer(s) 104.

In some implementations, image manager(s) 102, image viewer(s) 104, and/or image database(s) 120 may be operatively linked via one or more electronic communication links. For example, such electronic communication links may be established, at least in part, via a network, such as the Internet and/or other networks. It will be appreciated that this is not intended to be limiting, and the scope of this disclosure includes implementations in which image manager(s) 102, image viewer(s) 104, and/or image database(s) 120 may be operatively linked via some other communication media.

A given image viewer 104 may include one or more processors configured to execute computer program modules. The computer program modules may be configured to enable an expert or user associated with the given image viewer 104 to interface with system 100 and/or image database(s) 120, and/or provide other functionality attributed herein to image viewer(s) 104. By way of non-limiting example, a given image viewer 104 and/or a given image manager 102 may include one or more of a server, a desktop computer, a laptop computer, a handheld computer, a tablet computing platform, a Netbook, a Smartphone, a gaming console, and/or other computing platforms.

Image databases 120 may include sources of information outside of system 100, external entities participating with system 100, and/or other resources. Image manager(s) 102 may include electronic storage 122, one or more processors 124, and/or other components. Image manager(s) 102 may include communication lines or ports to enable the exchange of information with a network and/or other image managers. Illustration of image manager(s) 102 in FIG. 1 is not intended to be limiting. Image manager(s) 102 may include a plurality of hardware, software, and/or firmware components operating together to provide the functionality attributed herein to image manager(s) 102. For example, image manager(s) 102 may be implemented by a cloud of image managers operating together as image manager(s) 102.

Electronic storage 122 may comprise non-transitory storage media that electronically stores information. The electronic storage media of electronic storage 122 may include one or both of system storage that is provided integrally (i.e., substantially non-removable) with image manager(s) 102 and/or removable storage that is removably connectable to image manager(s) 102 via, for example, a port (e.g., a USB port, a firewire port, etc.) or a drive (e.g., a disk drive, etc.). Electronic storage 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 122 may include one or more virtual storage resources (e.g., cloud storage, a virtual private network, and/or other virtual storage resources). Electronic storage 122 may store software algorithms, information determined by processor(s) 124, information received from image manager(s) 102, information received from image viewer(s) 104, and/or other information that enables image manager(s) 102 to function as described herein.

Processor(s) 124 may be configured to provide information processing capabilities in image manager(s) 102. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1 as a single entity, this is for illustrative purposes only. In some implementations, processor(s) 124 may include a plurality of processing units. These processing units may be physically located within the same device or processor(s) 124 may represent processing functionality of a plurality of devices operating in coordination. Processor(s) 124 may be configured to execute modules 108, 110, and/or 114 and/or other modules. Processor(s) 124 may be configured to execute modules 108, 110, and/or 114, and/or other modules by software; hardware; firmware; some combination of software, hardware, and/or firmware; and/or other mechanisms for configuring processing capabilities on processor(s) 124. As used herein, the term "module" may refer to any component or set of components that perform the functionality attributed to the module. This may include one or more physical processors during execution of processor readable instructions, the processor readable instructions, circuitry, hardware, storage media, or any other components.

Although the present technology has been described in detail for the purpose of illustration based on what is currently considered to be the most practical and preferred implementations, it is to be understood such detail is solely for that purpose and the technology is not limited to the disclosed implementations, but, on the contrary, is intended to cover modifications and equivalent arrangements that are within the spirit and scope of the appended claims. For example, it is to be understood the present technology contemplates that, to the extent possible, one or more features of any implementation can be combined with one or more features of any other implementation.

The invention claimed is:

1. A method comprising:
identifying a set of image series of images from a plurality of image series that share the same frame of reference identifier;
grouping the image series in the set by axial planes, coronal planes, and sagittal planes of the images to create different groups of axial series, different groups of coronal series, and different groups of sagittal series, wherein the different groups of axial series are not a stack of images, wherein the different groups of axial series cannot be navigated in a linear manner through the images of the different groups of axial series;
wherein the grouping includes determining image instances from the image series of images in the set having the same plane and same coordinates to identify the different groups of axial series, the different groups of coronal series, and the different groups of sagittal series;
automatically creating links between image series in the different groups having image instances with the same plane and the same coordinates;
generating a linking graph from the image series of images in the set based on the automatically created links, wherein the linking graph links the different groups of the axial series together where two or more groups of axial series are linked, links the different groups of the coronal series together where two or more groups of coronal series are linked, and links the different groups of the sagittal series together where two or more groups of sagittal series are linked;
providing a user interface for manual synchronization that allows a user to select two or more image series to be linked together;
in response to the two or more image series being selected, manually creating one or more links in the linking graph that links the two or more image series that are selected;
wherein the linking graph is generated to include nodes representing image series that have been linked, and includes edges between the nodes that are linked representing a direction of relationships between the nodes;
receiving a selection from a user to view a first image series from the set, wherein a first image instance from the first image series is displayed in an active viewport;
accessing the linking graph to determine directly linked image series that are linked to the selected first image series by one edge in the linking graph, and an indirectly linked image series that is linked to the selected first image series by two edges in the linking graph, wherein the linking graph provides the direction of relationships between two or more different image series based on at least the edges defined in the linking graph;
comparing position coordinates of the first image instance in the active viewport to position coordinates of image instances of the directly linked image series to determine one or more linked image instances that have the same position coordinates as the first image instance;
determining an amount of change in image position needed to navigate to the determined image instance having the same position coordinates as the first image instance of a directly linked image series that lies between the first image series and the indirectly linked image series;
determining an indirectly linked image instance of the indirectly linked image series based on the determined amount of change;
automatically and simultaneously presenting the first image instance in the active viewport and displaying, in one or more non-active viewports, the one or more linked image instances from the directly linked image series that have the same position coordinates as the first image instance and the indirectly linked image instance from the indirectly linked image series on a graphical user interface (GUI); and
in response to a scrolling action that scrolls the first image instance in the active viewport to a second image instance in the first image series, automatically scrolling image instances in the one or more non-active viewports to display other image instances from the directly linked image series and the indirectly linked image series that have matching position coordinates as the second image instance in the active viewport.

2. The method of claim 1, further comprising:
comparing position coordinates of the second image instance from the first image series to position coordinates of image instances of the directly linked image series to determine the other image instances from the directly linked image series that have the same position coordinates as the second image instance from the first image series before the display of the other image instances from the directly linked image series that have matching position coordinates as the second image instance.

3. The method of claim 1, wherein the first image series and the linked image series are a collection of DICOM images.

4. The method of claim 1, wherein the first image series and the linked image series are from the same image study for a patient.

5. The method of claim 1, wherein the position coordinates comprise x, y, and z coordinates, image orientation, and row and column values from x, y, and z axes.

6. A method comprising:
identifying, from a plurality of image series, a set of image series of images that share the same frame of reference identifier;
identifying different groups of image series from the set of image series of images by axial planes, coronal planes, and sagittal planes of the images that form different groups of axial series, different groups of coronal series and different groups of sagittal series;
wherein the different groups of axial series are not a stack of images, wherein the different groups of axial series cannot be navigated in a linear manner through the images of the different groups of axial series;
automatically creating links between image series in the different groups having image instances with the same plane;
generating a linking graph from the set of image series based on the automatically created links, wherein the linking graph links the different groups of the axial series together, links the different groups of the coronal series together, and links the different groups of the sagittal series together;
providing a user interface for manual synchronization that allows a user to select two or more image series to be linked together;
in response to the two or more image series being selected, manually creating one or more links in the linking graph that links the two or more image series that are selected:
wherein the linking graph is generated to include nodes representing image series that have been linked, and includes edges between the nodes that are linked representing a direction of relationships between the nodes;
receiving a selection from a user to view a first image series from the set, wherein a first image instance from the first image series is displayed in an active viewport on a display device;
accessing the linking graph to determine directly linked image series that are linked to the selected first image series by one edge in the linking graph, and an indirectly linked image series that is linked to the selected first image series by two edges in the linking graph, wherein the linking graph provides the direction of relationships between two or more different image series based on at least the edges defined in the linking graph;
comparing position coordinates of the first image instance in the active viewport from the first image series to the position coordinates of image instances of the directly linked image series to determine one or more linked image instances that are the closest to the position coordinates of the first image instance from the first image series;
determining an amount of change in image position needed to navigate to the determined image instance having the closest position coordinates to coordinates of the first image instance of a directly linked image series that lies between the first image series and the indirectly linked image series:
determining an indirectly linked image instance of the indirectly linked image series based on the determined amount of change;
automatically and simultaneously presenting the first image instance in the active viewport and displaying, in one or more non-active viewports, the one or more linked image instances from the directly linked image series that have the closest position coordinates to coordinates of the first image instance and the indirectly linked image instance from the indirectly linked image series on a graphical user interface (GUI); and
in response to a scrolling action that scrolls the first image instance in the active viewport to a second image instance in the first image series, automatically scrolling image instances in the one or more non-active viewports to display other image instances from the directly linked image series and the indirectly linked image series that have closest position coordinates as the second image instance in the active viewport.

7. Non-transitory computer-readable media comprising computer-executable instructions embodied thereon that, when executed by at least a processor of a computing system cause the computing system to perform actions comprising:
identifying, from a plurality of image series including separately stored image series, a set of image series of images that share the same frame of reference identifier;
grouping the image series in the set by view planes including axial planes and coronal planes of the images to create different groups of axial series and different groups of coronal series;
wherein the different groups of axial series are not a stack of images, wherein the different groups of axial series cannot be navigated in a linear manner through the images of the different groups of axial series;
automatically creating links between images series in the different groups having image instances with the same plane;
generating a linking graph from the set of image series based on the automatically created links, wherein the linking graph links the different groups of the axial series together and links the different groups of the coronal series together;
providing a user interface for manual synchronization that allows a user to select two or more image series to be linked together;
in response to the two or more image series being selected, manually creating one or more links in the linking graph that links the two or more image series that are selected;

wherein the linking graph is generated to include nodes representing image series that have been linked, and includes edges between the nodes that are linked representing a direction of relationships between the nodes;

receiving a selection from a user to view a first image series from the set, wherein a first image instance from the first image series is displayed in an active viewport;

accessing the linking graph to determine directly linked image series that are linked to the selected first image series by one edge in the linking graph, and an indirectly linked image series that is linked to the selected first image series by two edges in the linking graph, wherein the linking graph provides the direction of relationships between two or more different image series based on at least the edges defined in the linking graph;

comparing position coordinates of the first image instance in the active viewport to position coordinates of image instances from the directly linked image series to determine one or more linked image instances that have the same position coordinates as the first image instance;

determining an amount of change in image position needed to navigate to the determined image instance having the same position coordinates as the first image instance of a directly linked image series that lies between the first image series and the indirectly linked image series;

determining an indirectly linked image instance of the indirectly linked image series based on the determined amount of change;

automatically and simultaneously presenting the first image instance in the active viewport and displaying, in one or more non-active viewports, the one or more linked image instances from the directly linked image series that have the same position coordinates as the first image instance and the indirectly linked image instance from the indirectly linked image series on a graphical user interface (GUI); and in response to a scrolling action that scrolls the first image instance in the active viewport to a second image instance in the first image series, automatically scrolling image instances in the one or more non-active viewports to display other image instances from the directly linked image series and the indirectly linked image series that have matching position coordinates as the second image instance in the active viewport.

8. The non-transitory computer-readable media of claim 7, further comprising computer-executable instructions that when executed cause the computing system to:

compare position coordinates of the second image instance from the first image series to position coordinates of image instances of the directly linked image series to determine the other image instances from the directly linked image series that have the same position coordinates as the second image instance from the first image series before the display of the other image instances from the directly linked image series that have matching coordinates as the second image instance.

9. The non-transitory computer-readable media of claim 7, wherein the first image series and the linked image series are a collection of DICOM images.

10. The non-transitory computer-readable media of claim 7, wherein the first image series and the linked image series are from the same image study for a patient.

11. The non-transitory computer-readable media of claim 7, wherein the position coordinates comprise x, y, and z coordinates, image orientation, and row and column values from x, y, and z axes.

* * * * *